United States Patent [19]

Wiker et al.

[11] Patent Number: 4,870,215

[45] Date of Patent: Sep. 26, 1989

[54] PHENOL ALKYLATION PROCESS

[75] Inventors: Steven L. Wiker; Charles W Matthews; Jeffrey F. King, all of Orangeburg, S.C.

[73] Assignee: Ethyl Corporation, Richmond, Va.

[21] Appl. No.: 211,295

[22] Filed: Jun. 24, 1988

[51] Int. Cl.$^4$ .............................................. C07C 37/14
[52] U.S. Cl. .................................... 568/789; 568/780; 568/794
[58] Field of Search ................................ 568/789, 794

[56] References Cited

U.S. PATENT DOCUMENTS

| | | | |
|---|---|---|---|
| 2,831,898 | 4/1958 | Ecke et al. | 568/789 |
| 3,355,504 | 11/1967 | Coffield et al. | 568/789 |
| 4,560,809 | 12/1985 | Goins et al. | 568/789 |

FOREIGN PATENT DOCUMENTS

| | | | |
|---|---|---|---|
| 2736059 | 2/1978 | Fed. Rep. of Germany | 568/794 |
| 0252439 | 12/1985 | Japan | 568/789 |
| 1200934 | 9/1986 | Japan | 568/789 |

*Primary Examiner*—Werren B. Lone
*Attorney, Agent, or Firm*—Joseph D. Odenweller

[57] ABSTRACT

Phenol is di-orthoalkylated in high yield by reacting, in a first stage, phenol containing only 1 mole of an aluminum phenoxide for each 100–800 moles of phenol with an olefin at 85°–175° C. until the reaction mixture contains 3 wt percent or less phenol and then, in a second stage, continuing the reaction at 25°–80° C. until the mixture contains a substantial amount of 2,6-di-alkylphenol.

12 Claims, No Drawings

PHENOL ALKYLATION PROCESS

BACKGROUND

Phenol can be selectively alkylated in an ortho position following the pioneering discovery of Ecke and Kolka, U.S. Pat. No. 2,831,898. According to U.S. Pat. No. '898, phenol containing an aluminum phenoxide is reacted with olefin at elevated temperature to produce an alkylation mixture containing substantial amounts of 2-alkylphenol and 2,6-dialkylphenol as well as other isomers.

Coffield et al., U.S. Pat. No. 3,355,504, describe an improvement in the orthoalkylation process wherein 2,6-di-alkylphenols are made in high yield under moderate conditions by starting the process with 2-alkylphenol containing an aluminum 2-alkylphenoxide and reacting this mixture with an olefin. If the 2-alkylphenol is made by the aluminum phenoxide catalyzed alkylation of phenol, then additional aluminum phenoxide forming compound must be added to be in molar excess of any remaining phenol or phenol ethers before conducting the second alkylation.

SUMMARY OF THE INVENTION

It has now been discovered that 2,6-di-alkylphenols can be made in high yield from phenol by first alkylating phenol which contains only about 1 gram atom of aluminum as a phenoxide per 100-800 moles or more of phenol until phenol content is 3 wt percent or less and then lowering the temperature and continuing the alkylation to obtain 2,6-dialkylphenol in improved yield while reducing the 2-alkylphenol and 2,4-dialkylphenol content of the reaction product. Addition of additional aluminum phenoxide forming compound after the first stage to consume residual phenol is not required.

DESCRIPTION OF THE PREFERRED EMBODIMENTS

A preferred embodiment of the invention is a process for selectively di-orthoalkylating phenol, said process comprising:

(A) introducing an aluminum phenoxide into said phenol in an amount that provides about 1 gram mole of aluminum phenoxide per each 100-800 gram moles of phenol, (B) in a first stage, introducing olefin into said phenol in an amount sufficient to at least mono-alkylate all of said phenol and reacting the mixture at about 85°-175° C. until the non-alkylated phenol in said mixture is lowered such that it is 3 wt percent or less of said mixture, (C) cooling said mixture to about 25°-80° C., (D) in a second stage, introducing additional olefin, if required, such that the total olefin added is at least 1.75 moles per mole of said phenol, (E) continuing the reaction in said second stage at 25°-80°C. until said mixture contains a substantial amount of 2,6-dialkylphenol and (F) recovering said 2,6-di-alkylphenol.

The aluminum phenoxide catalyst can be introduced into the phenol in any manner. It can be separately prepared and added to the phenol. Alternatively aluminum metal can be added directly to the phenol in the proper amount and the mixture stirred and heated to cause phenoxide formation. A reactive aluminum compound such as aluminum hydride, trimethyl aluminum, triethyl aluminum, diethyl aluminum hydride, diethyl aluminum chloride, triisobutyl aluminum and the like can be added to react with phenol and form an aluminum phenoxide catalyst.

The phenol is preferably dry but need not be bone-dry. Water content up to 0.05% is acceptable although it is preferred to keep water content under 0.03 wt %. Commercial grade phenol is available for use in the process.

Olefins used in the process include any olefin capable of alkylating phenol such as ethylene, propylene, isobutylene, 1-butene, 2-pentene, 2-ethyl-1-hexene, 1-dodecene, cyclohexene, styrene, $\alpha$-methyl styrene, cyclopentene and the like. The preferred olefins are the monounsaturated aliphatic hydrocarbons containing 2-12 carbon atoms. The most preferred olefin is isobutylene.

In a conventional aluminum phenoxide catalyzed orthox alkylation of phenol, the amount of aluminum phenoxide catalyst is about 1 mole for each 20-30 moles of phenol. In the present process the quantity of catalyst is greatly reduced to only about 1 gram mole of aluminum phenoxide (equal to 1 gram atom of aluminum) for each 100-800 gram moles of phenol. This represents only 0.001-0.01 mole percent aluminum phenoxide. The preferred amount of catalyst is 1 gram mole for each 150-500 moles of phenol and, most preferably, 1 mole of aluminum phenoxide for each 180-300 moles of phenol.

The aluminum phenoxide can be readily formed by merely adding clean aluminum metal to the phenol in an autoclave, sealing the autoclave and heating to about 150° C. to cause the aluminum to react to form aluminum phenoxide. A preferred way to prepare the catalyst is to add a reactive aluminum compound such as an alkyl aluminum (e.g. triethyl aluminum) and heating the stirred mixture to about 150° C. to form the aluminum phenoxide.

If the phenol is wet, part of the aluminum or alkyl aluminum will react to form aluminum oxide or hydroxide. Likewise if the olefin is wet or water is accidentally left in the reactor, some aluminum phenoxide will be hydrolyzed. Hence the amount of aluminum or reactive aluminum compound added will be higher than the amount required to form the amount of aluminum phenoxide desired in the reaction mixture. When the term "aluminum phenoxide" is used herein it means the actual aluminum phenoxide formed excluding that hydrolyzed and not the amount of aluminum or reactive aluminum compound added. Of course with bone-dry phenol and olefin containing no reactive hydrogen other than the phenolic hydroxyl, these will be the same. Additional aluminum or reactive aluminum compound (e.g. triethyl aluminum) may be necessary to counteract any water in wet phenol or olefin. Three moles of water will theoretically react with one mole of triethyl aluminum, but even one mole of water per mole of aluminum inhibits catalyst activity.

Olefin is added to the first stage reaction in an amount which is sufficient to at least monoalkylate all the phenol in the reactor. A useful range in which to operate is about 1.5-2.5 moles of olefin per mole of phenol. This olefin can all be added at the start of the first stage reaction or can be fed continuously or incrementally during the course of the first stage. The preferred amount of olefin added in the first stage is about 1.9-2.4 moles and more preferably 2.0-2.25 moles per mole of phenol.

The rate of adding the olefin to the first stage is usually limited by cooling capacity. Faster feed gives better results as long as the temperature can be controlled. A preferred temperature range is about 85°–175° C. A more preferred temperature range is about 100°–150° C. The most preferred first stage temperature is about 110°–125° C.

Pressure rises as olefin is added. The pressure will generally be in the range of 50–1000 psig. A preferred pressure is about 100–500 psig. The composition of the reaction mixture can be monitored by gas chromatography (GC). The first stage is continued until the phenol content of the reaction mixture drops to 3 wt % or less. Preferably the phenol will be lowered to 2 weight percent or less. The more preferred phenol target is 1–2 wt % percent range with 1% or less being highly preferred. This usually requires about 1–4 hours.

The reaction temperature is then lowered into the range of 25°–80° C. for the second stage of the reaction. A more preferred second stage temperature is 50°–70° C. At this time additional olefin can be added, if needed, to complete the alkylation and maximize yield of 2,6-di-tert-butylphenol. If sufficient olefin was added during the first stage it will not be necessary to add more olefin for the second stage. The total olefin added in both stages is preferably at least 1.75 moles and more preferably at least 2 moles (e.g. 2–2.4 moles) per mole of phenol charged. A more preferred total olefin is about 2–2.25 moles per mole of initial phenol. If the desired amount of olefin was not added in the first stage, the shortfall can be made up in the second stage. In this mode of operation, up to about 10 mole percent, e.g. 5–10 mole %, of the total olefin feed is added between the first and second stages or during the second stage or both.

Surprisingly it was found that when operating as described, even with the very low concentration of aluminum phenoxide added at the start of the first stage, it is not necessary and in fact is undesirable to add more catalyst prior to the second stage to consume residual phenol.

The second stage reaction is then continued in the range of 25°–80° C., more preferably 50°–70° C., while monitoring composition by gas chromatography, GC. The 2,6-dialkylphenol concentration will gradually increase as the 2-alkylphenol decreases. When optimized the concentration of 2,6-dialkylphenol will be at least 75 wt percent and preferably at least 80 wt percent. The second stage reaction usually requires about 1–24 hours.

Following the second stage, the catalyst is deactivated and removed from the reaction mixture by well-known methods such as water-washing, flash distillation, filtration and the like. More preferably, the reaction mixture is water-washed to remove aluminum. This is preferably done under acidic conditions to avoid gel. The washed reaction mixture can then be distilled to recover 2,6-dialkylphenol. Light ends (e.g., phenol and 2-alkylphenol) can be recycled back to the next first stage reaction as part of the phenol charge. Bottoms (e.g., 2,4-dialkylphenol and 2,4,6-trialkylphenol) can be dealkylated and then recycled to a subsequent reaction cycle.

The following examples show how the process is conducted. All parts are by weight.

EXAMPLE 1

In a reactor was placed 19364 parts (206 moles) of phenol. The reactor was flushed with nitrogen and while stirring 114 parts (1 moles) of triethyl aluminum were added. The reactor was sealed and the mixture was reacted for 30 minutes to form aluminum triphenoxide. Then heat was applied while pumping isobutylene into the reactor. As the reaction became exothermic cooling was applied to hold the temperature in the range of 115°–125° C. Total isobutylene feed was 24282 parts over a 45 minute period. The maximum pressure was about 300 psig. Stirring was continued at about 115° C. as isobutylene reaction continued causing the pressure to drop to 105 psig over a 1½ hour period. Analysis by GC showed the phenol content at this time to be 0.7 wt percent.

Cooling was applied and the reaction temperature dropped to 70° C. Stirring was continued at 70° C. for 4 hours. The reaction mixture was analyzed by GC and the composition is shown in the later table.

EXAMPLE 2

In a reaction vessel was placed 8100 parts of phenol and 27 parts of aluminum metal. The vessel was sealed and heated to 150° C. to form aluminum triphenoxide. This catalyst concentrate was then mixed with 11,124 parts of additional phenol. This gives a phenol-/aluminum mole ratio of about 203. The phenol-catalyst mixture was cooled to 90° C. and 23,490 parts of isobutylene was pumped in over a 50-minute period. The reaction temperature rose to 110° during the first 10 minutes of isobutylene feed. Stirring was continued at 110°–115° C. for 165 minutes. Reactor pressure dropped to 120 psig from a maximum of 260 psig.

Cooling was then applied to lower the temperature to 0° C. over a 45-minute period. An additional 728 parts of isobutylene was then pumped in and the reaction mixture stirred for an additional 90 minutes at 70° C. The reaction mixture composition is shown in the later table.

Following is a phenol alkylation conducted by a conventional method for comparative purposes.

EXAMPLE 3

In a reactor was placed 2820 parts (30 moles) of phenol. The reactor was flushed with nitrogen and while stirring, 114 parts (1 mole) of triethyl aluminum was added. The reactor was stirred for 30 minutes to form the aluminum phenoxide catalyst and then sealed. While heating 3360 parts (60 moles) of isobutylene was pumped in over a 75-minute period. As the reaction became exothermic cooling was applied to control the temperature at 100° C. After completion of isobutylene feed the mixture was stirred for 4 hours at 100° C. during which time the pressure dropped from 300 psig to 80 psig. The reaction mixture was then washed with acidic water to remove aluminum. The mixture composition is shown in the following table.

| Component | Example 1 | Example 2 | Example 3 |
| --- | --- | --- | --- |
| 2,6-di-tert-butylphenol | 82.5 | 82.7 | 73.3 |
| 2-tert-butylphenol | 2.5 | 2.0 | 9.5 |
| 2,4-di-tert-butylphenol | 0.6 | 0.4 | 1.6 |
| 2,4,6-tri-tert-butylphenol | 12.7 | 13.2 | 10.7 |
| 4-tert-butylphenol | — | — | .1 |
| 2-tert-octylphenol | 0.8 | 0.6 | .8 |
| 2-tert-butylphenyl tert-butyl ether | 0.8 | 1.0 | 1.0 |
| phenol | 0.1 | 0.1 | 3.0 |

These results show that the new process gives a sharp increase in yield of 2,6-di-tert-butylphenol while decreasing the amount of 2-tert-butylphenol and 2,4-ditert-butylphenol giving the new process a distinct economic advantage over the conventional process.

We claim:

1. A process for selectively di-orthoalkylating phenol, said process comprising:
   (A) introducing an aluminum phenoxide into said phenol in an amount that provides about 1 gram mole of aluminum phenoxide per each 100–800 gram moles of phenol,
   (B) in a first stage, introduce phenol in an amount sufficient to at least mono-alkylate all of said phenol and reacting the mixture at about 85°–175° C. until the non-alkylated phenol in said mixture is lowered such that it is 3 wt percent or less of said mixture,
   (C) cooling said mixture to about 25°–80° C.,
   (D) in a second stage, introducing additional olefin, if required, such that the total olefin added is at least 1.75 moles per mole of said phenol,
   (E) continuing the reaction in said second stage at 25°–80° C. until said mixture contains a substantial amount of 2,6-dialkylphenol and
   (F) recovering said 2,6-di-alkylphenol.

2. A process of claim 1 further characterized in that additional aluminum phenoxide forming compound is not added between said first and said second stages to consume residual phenol.

3. A process of claim 2 wherein said olefin is isobutylene.

4. A process of claim 3 wherein said first stage is conducted at 100°–150° C. at a pressure of about 50–1000 psig.

5. A process of claim 4 wherein the amount of aluminum phenoxide provides about 1 gram atom of aluminum for each 150–500 gram moles of said phenol.

6. A process of claim 5 wherein said second stage is conducted at a temperature of about 50°–70°C.

7. A process of claim 5 wherein the total isobutylene added is about 2.0–2.25 moles per mole of said phenol.

8. A process of claim 7 wherein all of said isobutylene is added in said first stage.

9. A process of claim 7 wherein about 85–95 percent of said isobutylene is added in said first stage and the remaining isobutylene is added between said first and second stages or during said second stage.

10. A process of claim 7 wherein said first stage is conducted until said non-alkylated phenol does not exceed 3 wt percent.

11. A process for making 2,6-di-tert-butylphenol in high yield while minimizing 2-tert-butylphenol and 2,4-di-tertiary butylphenol content of the product, said process comprising:
    (A) introducing an aluminum phenoxide into said phenol in an amount to provide about 1 gram atom of aluminum for each 180–300 gram moles of phenol,
    (B) in a first stage, introducing about 2.0–2.25 gram moles of isobutylene and reacting the mixture at 110°–125° C., until the phenol content does not exceed 3 wt percent,
    (C) cooling the mixture to 50°–70° C.,
    (D) in a second stage, continuing the reaction at 50°–70° C. without adding additional aluminum phenoxide forming compound until the reaction mixture contains at least 75 wt percent 2,6-di-tert-butylphenol and
    (E) recovering said 2,6-di-tert-butylphenol.

12. A process of claim 11 wherein a portion of said isobutylene, up to about 10 mole percent, is added between said first and second stages or during said second stage.

* * * * *

UNITED STATES PATENT AND TRADEMARK OFFICE
CERTIFICATE OF CORRECTION

PATENT NO. : 4,870,215

DATED : SEPTEMBER 26, 1989

INVENTOR(S) : STEVEN L. WIKER ET AL.

It is certified that error appears in the above-identified patent and that said Letters Patent is hereby corrected as shown below:

Column 5, line 11 reads "introduce phenol" and should read -- introducing olefin into said phenol -- .

Signed and Sealed this

Twenty-fifth Day of September, 1990

Attest:

HARRY F. MANBECK, JR.

*Attesting Officer*  *Commissioner of Patents and Trademarks*